(12) United States Patent
Gallou et al.

(10) Patent No.: US 9,006,270 B2
(45) Date of Patent: Apr. 14, 2015

(54) POLYMORPHS OF (S)-PYRROLIDINE-1,2-DICARBOXYLIC ACID 2-AMIDE 1-({4-METHYL-5-[2-(2,2,2-TRIFLUORO-1,1-DIMETHYL-ETHYL)-PYRIDIN-4-YL]-THIAZOL-2-YL}-AMIDE

(75) Inventors: Isabelle Sylvie Gallou, Binningen (CH); Cornelius Gauer, Reinach (CH); Frank Stowasser, Murg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/127,027

(22) PCT Filed: Jun. 19, 2012

(86) PCT No.: PCT/EP2012/061756
§ 371 (c)(1),
(2), (4) Date: Dec. 17, 2013

(87) PCT Pub. No.: WO2012/175522
PCT Pub. Date: Dec. 27, 2012

(65) Prior Publication Data
US 2014/0171470 A1 Jun. 19, 2014

Related U.S. Application Data

(60) Provisional application No. 61/499,222, filed on Jun. 21, 2011.

(51) Int. Cl.
C07D 417/14 (2006.01)

(52) U.S. Cl.
CPC .................................... *C07D 417/14* (2013.01)

(58) Field of Classification Search
None
See application file for complete search history.

(56) References Cited

FOREIGN PATENT DOCUMENTS

| WO | 2010029082 A1 | 3/2010 |
|---|---|---|
| WO | 2012/016970 A1 | 2/2012 |

*Primary Examiner* — Timothy R Rozof
(74) *Attorney, Agent, or Firm* — Sandra Rueck

(57) ABSTRACT

The present invention relates to specific solid forms of (S)-pyrrolidine-1,2-dicarboxylic acid 2-amide 1-(4-methyl-5-[2-(2,2,2-trifluoro-1,1-dimethyl-ethyl)-pyridin-4-yl]-thiazol-2-yl)-amide, and its solvates. The present invention further relates to processes for preparing said solid forms, pharmaceutical compositions comprising said solid forms, and methods of using said solid forms and pharmaceutical compositions to treat disease.

15 Claims, 7 Drawing Sheets

POLYMORPHS OF (S)-PYRROLIDINE-1,2-DICARBOXYLIC ACID 2-AMIDE 1-({4-METHYL-5-[2-(2,2,2-TRIFLUORO-1,1-DIMETHYL-ETHYL)-PYRIDIN-4-YL]-THIAZOL-2-YL}-AMIDE

FIELD OF THE INVENTION

The present invention relates to specific solid forms of (S)-pyrrolidine-1,2-dicarboxylic acid 2-amide 1-(4-methyl-5-[2-(2,2,2-trifluoro-1,1-dimethyl-ethyl)-pyridin-4-yl]-thiazol-2-yl)-amide, and its solvates. The present invention further relates to processes for preparing said solid forms, pharmaceutical compositions comprising said solid forms, and methods of using said solid forms and pharmaceutical compositions to treat disease.

BACKGROUND (S)-pyrrolidine-1,2-dicarboxylic acid 2-amide 1-(4-methyl-5-[2-(2,2,2-trifluoro-1,1-dimethyl-ethyl)-pyridin-4-yl]-thiazol-2-yl)-amide, hereafter referred to as compound I,

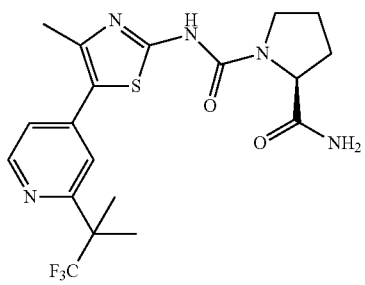

(I)

is an alpha-selective phosphatidylinositol 3-kinase (PI3K) inhibitor. Compound I was originally described in WO 2010/029082, wherein the synthesis of its free base form was described. There is a need for additional solid forms of compound I, for use in drug substance and drug product development. It has been found that new solid forms of compound I can be prepared as one or more polymorph forms, including solvate forms. These polymorph forms exhibit new physical properties that may be exploited in order to obtain new pharmacological properties, and that may be utilized in drug substance and drug product development.

SUMMARY OF THE INVENTION

In one aspect, provided herein is a crystalline form of the compound of formula I, or a solvate of the crystalline form of the compound of formula I, or a salt of the crystalline form of the compound of formula I, or a solvate of a salt of the crystalline form of the compound of formula I. In one embodiment, the crystalline form of the compound of formula I has the polymorph form $S_A$, $S_B$, $S_C$, or $S_D$.

In another aspect, provided herein is a pharmaceutical composition comprising a crystalline compound of formula I. In one embodiment of the pharmaceutical composition, the crystalline compound of formula I has the polymorph form $S_A$, $S_B$, $S_C$, or $S_D$.

In another aspect, provided herein is a method for the treatment of disorders mediated by PI3K, comprising administering to a patient in need of such treatment an effective amount of a crystalline compound of formula I, particularly $S_A$, $S_B$, $S_C$, or $S_D$.

In yet another aspect, provided herein is the use of a crystalline compound of formula I, particularly $S_A$, $S_B$, $S_C$, or $S_D$, for the preparation of a medicament for the treatment of disorders mediated by PI3K.

In still another aspect, provided herein is a method for the treatment of disorders selected from benign or malignant tumor; a cancer selected from sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and Walden stroem disease; as well as polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g., haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma, comprising administering to a patient in need of such treatment an effective amount of the crystalline compound of formula I, particularly polymorph forms $S_A$, $S_B$, $S_C$, or $S_D$.

In another aspect, provided herein is the use of the crystalline compound of formula I, particularly polymorph forms $S_A$, $S_B$, $S_C$, or $S_D$, for the preparation of a medicament for the treatment of the disorders listed above.

DETAILED DESCRIPTION OF THE INVENTION

Polymorph Forms and Properties

Figure 1:
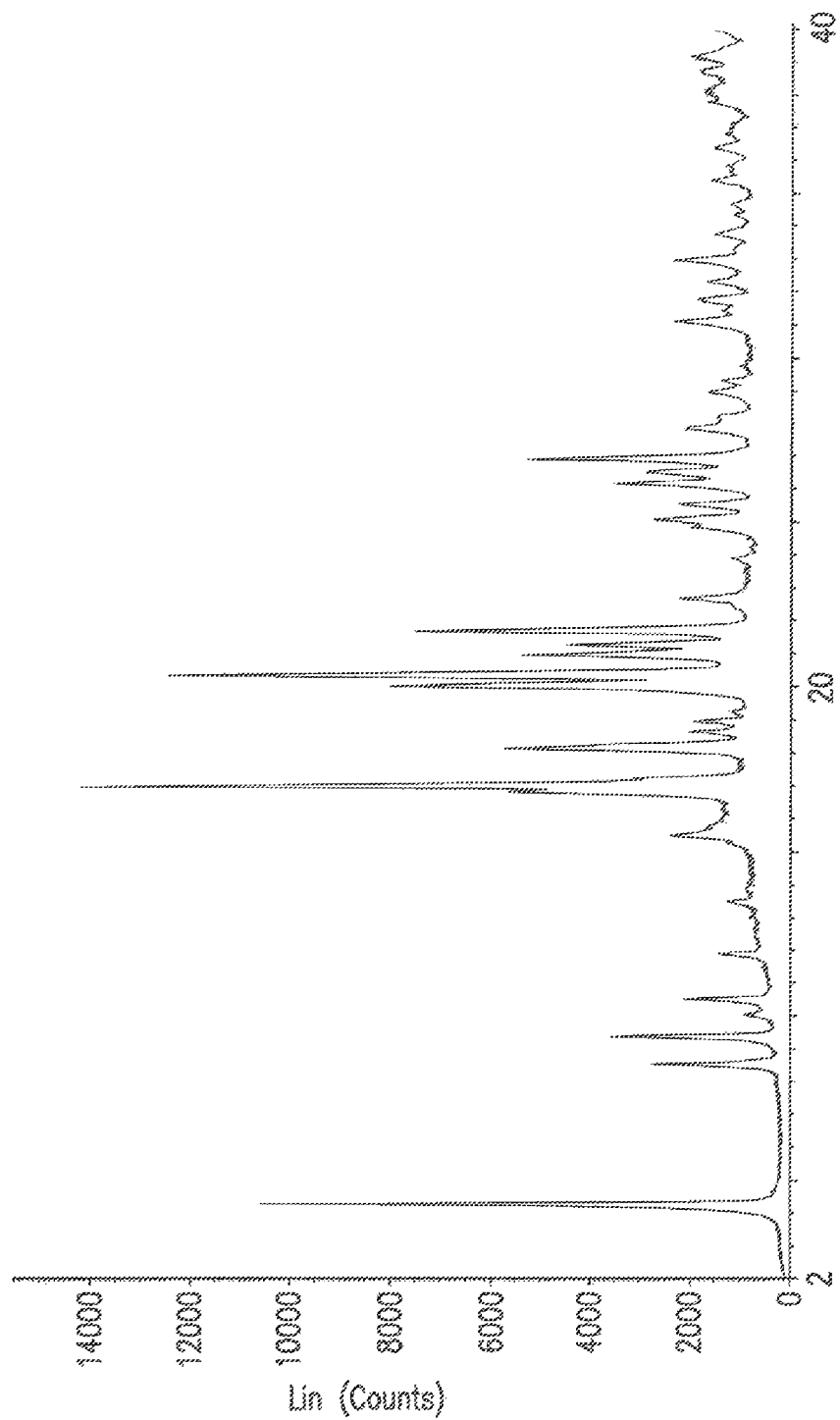
FIG. 1 (also referenced as FIG. I) depicts the X-ray powder diffraction pattern of polymorph form A.

The present invention relates to crystalline forms of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide). (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), also referred to as the compound of formula I, or Compound I, was originally described in WO 2010/029082, the contents of which are incorporated herein by reference. Compound I is an inhibitor of PI3K (phosphatidylinositol 3-kinase), and shows an improved selectivity for PI3K alpha with respect to beta, delta and gamma subtypes in biochemical, as well as cellular, assays. Accordingly, Compound I, and pharmaceutical compositions comprising Compound I, can be used for the prevention, amelioration or treatment of diseases depending on PI3K (in particular PI3K alpha). As described herein, the free base of Compound I can be a crystalline form that exists as one or more polymorph forms, including solvate forms. These polymorph forms (alternatively known in the art as polymorphic forms or crystal forms) differ with respect to their X-ray powder diffraction patterns, spectroscopic, physicochemical and pharmacokinetic properties, as well as their thermodynamic stability.

It is desirable to have access to different polymorph forms of crystalline Compound I, its solvates, its salts and solvates of its salts for several reasons. For example, distinct polymorph forms may incorporate distinct impurities upon crystallization, i.e. an impurity incorporated in polymorph form A is not necessarily also incorporated in the polymorph forms $S_A$, $S_B$, $S_C$ or $S_D$. Thus, the iterative preparation of distinct polymorph forms of Compound I may be used to increase the purity of the finally obtained form. In addition, distinct polymorph forms may exhibit different physical properties such as melting point, hygroscopicity, solubility, flow properties or thermodynamic stability, and therefore, distinct polymorph forms allow the choice of the most suitable form for a given use or aspect, e.g., the use as an intermediate in the process of drug manufacture, in distinct administration forms such as tablets, capsules, ointments, suspensions or solutions, or in the manufacture of a drug form having optimum pharmacokinetic properties.

Thus, in one aspect, provided herein is a crystalline form of the compound of formula I, or a solvate of the crystalline form of the compound of formula I, or a salt of the crystalline form of the compound of formula I, or a solvate of a salt of the crystalline form of the compound of formula I.

The compound of formula I may have polymorph form A. Polymorph form A can be defined by reference to one or more characteristic signals that result from analytical measurements including, but not necessarily limited to: the X-ray powder diffraction pattern of FIG. 1, the FT-IR spectrum of FIG. 2, or the differential scanning calorimetry thermogram of FIG. 3. Polymorph form A can also be defined by reference to one or more of the following characteristic signals:

The polymorph form A exhibits an X-ray powder diffraction pattern having characteristic peaks expressed in degrees 2-Theta at angles of 17.1°+/−0.3° and 20.4°+/−0.3°. In yet another embodiment, the polymorph form A exhibits characteristic peaks at angles of 4.2°+/−0.3° and 21.7°+/−0.3°. In still another embodiment, the polymorph form A exhibits characteristic peaks at angles of 18.2°+/−0.3° and 20.1°+/−0.3°. In another embodiment, the polymorph form A exhibits characteristic peaks at angles of 17.1°+/−0.3°, 20.4°+/−0.3°, 4.2°+/−0.3°, 21.7°+/−0.3°, 18.2°+/−0.3° and 20.1°+/−0.3°. In a further embodiment, the polymorph form A exhibits an X-ray powder diffraction pattern substantially in accordance with FIG. 1 and Table 1.

Figure 2:
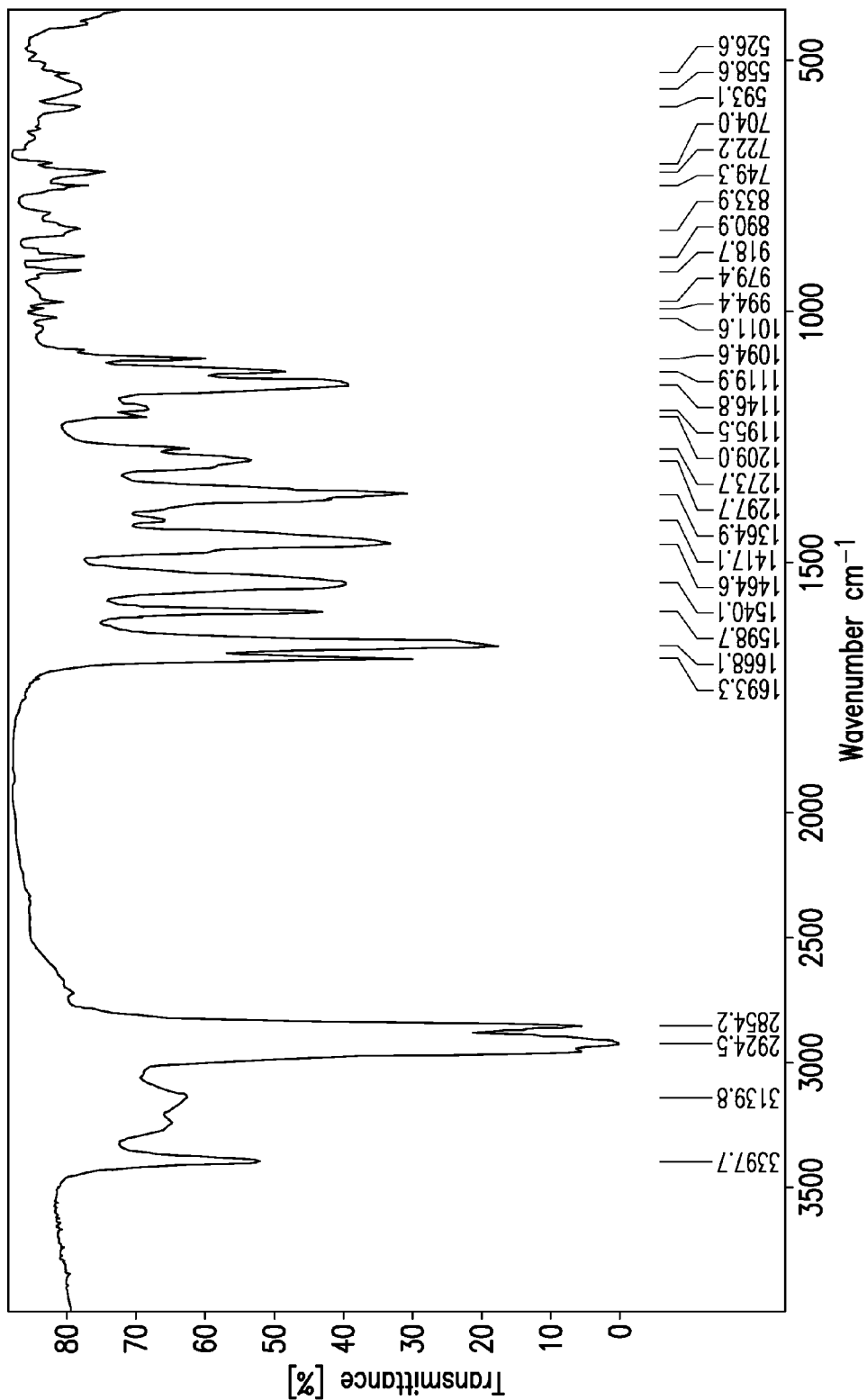
FIG. 2 (also referenced as FIG. II) depicts the FT-IR spectrum of polymorph form A.
Figure 3:
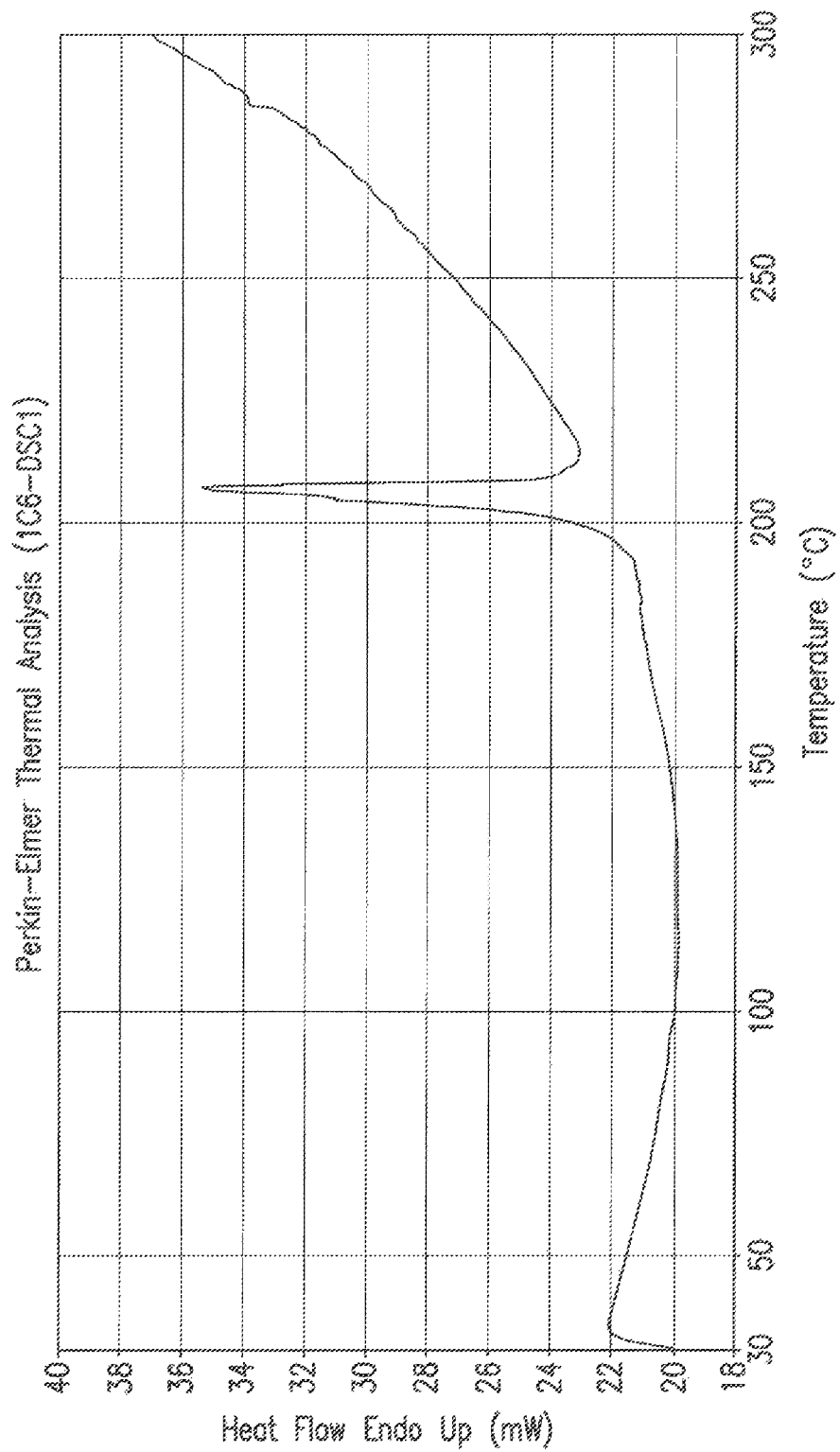
FIG. 3 (also referenced as FIG. III) depicts the differential scanning calorimetry thermogram of polymorph form A.

The polymorph form A exhibits an FT-IR spectrum having characteristic peaks expressed in units of $cm^{-1}$ at values of about 1693 and about 1668. In another embodiment, the polymorph form A exhibits additional peaks at values of about 1599 and about 1540. In still another embodiment, the polymorph form A exhibits an FT-IR spectrum substantially in accordance with FIG. 2 with exception of the additional peaks of about 2925 and 2854. FIG. 2 of the present application includes additional peaks of about 2925 and 2854 which correspond to the Nujol® mineral oil (Schering-Plough Corporation) used in the FT-IR measurement.

The polymorph form A exhibits a differential scanning calorimetry thermogram having a characteristic peak expressed in units of ° C. at a temperature of about 203. In another embodiment, the polymorph form A exhibits a differential scanning calorimetry thermogram substantially in accordance with FIG. 3.

In one embodiment of the present invention, the compound of formula I has the polymorph form $S_A$. Polymorph form $S_A$ is a specific solvate of the compound of formula I which can be defined by reference to one or more characteristic signals that result from analytical measurements including, but not necessarily limited to, the X-ray powder diffraction pattern of FIG. 4. Polymorph form $S_A$ can also be defined by reference to one or more of the following characteristic signals:

In one embodiment, the polymorph form $S_A$ exhibits an X-ray powder diffraction pattern having characteristic peaks expressed in degrees 2-Theta at angles of 16.9°+/−0.3° and 17.7°+/−0.3°. In another embodiment, the polymorph form $S_A$ exhibits an X-ray powder diffraction pattern having characteristic peaks expressed in degrees 2-Theta at angles of 13.3°+/−0.3° and 18.2°+/−0.3°. In yet another embodiment, the polymorph form $S_A$ exhibits an X-ray powder diffraction pattern having characteristic peaks expressed in degrees 2-Theta at angles of 20.3°+/−0.3° and 16.5°+/−0.3°. In still another embodiment, the polymorph form $S_A$ exhibits an X-ray powder diffraction pattern having characteristic peaks expressed in degrees 2-Theta at angles of 16.9°+/−0.3°, 17.7°+/−0.3°, 13.3°+/−0.3°, 18.2°+/−0.3°, 20.3°+/−0.3° and 16.5°+/−0.3°. In a further embodiment, the polymorph form $S_A$ exhibits an X-ray powder diffraction pattern substantially in accordance with FIG. 4 and Table 2.

In one embodiment, the compound of formula I has the polymorph form $S_B$. Polymorph form $S_B$ is another specific solvate of the compound of formula I which can be can be defined by reference to one or more characteristic signals that result from analytical measurements including, but not necessarily limited to, the X-ray powder diffraction pattern of FIG. 5. Polymorph form $S_B$ can also be defined by reference to one or more of the following characteristic signals:

In one embodiment, the polymorph form $S_B$ exhibits an X-ray powder diffraction pattern having characteristic peaks expressed in degrees 2-Theta at angles of 13.2°+/−0.3° and 18.3°+/−0.3°. In another embodiment, the polymorph form $S_B$ exhibits an X-ray powder diffraction pattern having characteristic peaks expressed in degrees 2-Theta at angles of 17.0°+/−0.3° and 15.7°+/−0.3°. In yet another embodiment, the polymorph form $S_B$ exhibits an X-ray powder diffraction pattern having characteristic peaks expressed in degrees 2-Theta at angles of 20.4°+/−0.3° and 16.4°+/−0.3°. In still another embodiment, the polymorph form $S_B$ exhibits an X-ray powder diffraction pattern having characteristic peaks expressed in degrees 2-Theta at angles of 13.2°+/−0.3°, 18.3°+/−0.3°, 17.0°+/−0.3°, 15.7°+/−0.3°, 20.4°+/−0.3° and 16.4°+/−0.3°. In a further embodiment, the polymorph form $S_B$ exhibits an X-ray powder diffraction pattern substantially in accordance with FIG. 5 and Table 3.

In one embodiment, the compound of formula I has the polymorph form $S_C$. Polymorph form $S_C$ is another specific solvate of the compound of formula I which can be can be defined by reference to one or more characteristic signals that result from analytical measurements including, but not necessarily limited to, the X-ray powder diffraction pattern of FIG. 6. Polymorph form $S_C$ can also be defined by reference to one or more of the following characteristic signals:

In one embodiment, the polymorph form $S_C$ exhibits an X-ray powder diffraction pattern having characteristic peaks expressed in degrees 2-Theta at angles of 17.0°+/−0.3° and 18.2°+/−0.3°. In another embodiment, the polymorph form $S_C$ exhibits an X-ray powder diffraction pattern having characteristic peaks expressed in degrees 2-Theta at angles of 16.5°+/−0.3° and 13.2°+/−0.3°. In yet another embodiment, the polymorph form $S_C$ exhibits an X-ray powder diffraction pattern having characteristic peaks expressed in degrees 2-Theta at angles of 14.5°+/−0.3° and 15.6°+/−0.3°. In still another embodiment, the polymorph form $S_C$ exhibits an X-ray powder diffraction pattern having characteristic peaks expressed in degrees 2-Theta at angles of 17.0°+/−0.3°, 18.2°+/−0.3°, 16.5°+/−0.3°, 13.2°+/−0.3°, 14.5°+/−0.3° and 15.6°+/−0.3°. In a further embodiment, the polymorph form $S_C$ exhibits an X-ray powder diffraction pattern substantially in accordance with FIG. 6 and Table 4.

In one embodiment, the compound of formula I has the polymorph form $S_D$. Polymorph form $S_D$ is another specific solvate of the compound of formula I which can be can be defined by reference to one or more characteristic signals that result from analytical measurements including, but not necessarily limited to, the X-ray powder diffraction pattern of FIG. 7. Polymorph form $S_D$ can also be defined by reference to one or more of the following characteristic signals:

In one embodiment, the polymorph form $S_D$ exhibits an X-ray powder diffraction pattern having characteristic peaks expressed in degrees 2-Theta at angles of 9.3°+/−0.3° and 3.5°+/−0.3°. In another embodiment, the polymorph form $S_D$ exhibits an X-ray powder diffraction pattern having characteristic peaks expressed in degrees 2-Theta at angles of 7.0°+/−0.3° and 4.9°+/−0.3°. In yet another embodiment, the polymorph form $S_D$ exhibits an X-ray powder diffraction pattern having characteristic peaks expressed in degrees 2-Theta at angles of 18.1°+/−0.3° and 20.8°+/−0.3°. In still another embodiment, the polymorph form $S_D$ exhibits an X-ray powder diffraction pattern having characteristic peaks expressed in degrees 2-Theta at angles of 9.3°+/−0.3°, 3.5°+/−0.3°, 7.0°+/−0.3°, 4.9°+/−0.3°, 18.1°+/−0.3° and 20.8°+/−0.3°. In a further embodiment, the polymorph form $S_D$ exhibits an X-ray powder diffraction pattern substantially in accordance with FIG. 7 and Table 5.

In one embodiment, the polymorph form $S_A$, $S_B$, $S_C$, or $S_D$ contains less than 10% by weight total impurities. In another embodiment, the polymorph form $S_A$, $S_B$, $S_C$, or $S_D$ contains less than 5% by weight total impurities. In yet another embodiment, the polymorph form $S_A$, $S_B$, $S_C$, or $S_D$ contains less than 2% by weight total impurities.

As used herein, the term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like.

Preparation

As discussed above, the present invention relates also to a process for the preparation of solid, preferably crystalline, forms of the compound of formula I, its solvates, its salts and solvates of its salts. The precise conditions under which specific polymorphs are formed can be determined empirically and a number of methods are suitable in practice, including the crystallization conditions as described herein.

The polymorph form A of the compound of formula I may be prepared by a process comprising the following steps: (a) dissolving a compound of formula I in 50-90% aqueous acetone, (b) adding water to achieve lower solubility, and (c) keeping the temperature above 30° C. to form the polymorph form A. Preferably, the compound of formula I is dissolved in 70% aqueous acetone in the above described step (a).

In one embodiment of the process, the temperature is in the range of 30-70° C.

In another embodiment of the process, the temperature is in the range of 30-60° C.

In yet another embodiment of the process, the temperature is in the range of 50-55° C.

In still another embodiment of the process, the mixture is seeded with one or more crystals of polymorph form A.

As used herein, the term "seed" can be used as a noun to describe one or more crystals of a crystalline compound of formula I. The term "seed" can also be used as a verb to describe the act of introducing said one or more crystals of a crystalline compound of formula I into an environment (including, but not limited to e.g., a solution, a mixture, a suspension, or a dispersion) thereby resulting in the formation of more crystals of the crystalline compound of formula I.

The polymorph form $S_A$, $S_B$, $S_C$, and $S_D$ may be prepared by the process set forth in Examples 4 to 7 herein.

Methods of Treatment

The present invention also provides a method for preventing, ameliorating or treating conditions, disorders or diseases mediated by the activation of PI3K, especially PI3Kα, e.g., such as indicated above, in a subject in need of such treatment, which method comprises administering to said subject an effective amount of a crystalline compound of formula I, especially polymorph forms $S_A$, $S_B$, $S_C$, or $S_D$.

The PI3K pathway is activated by several different mechanisms in cancers, as described, for example, by Engelman et al. (J. Clin. Oncol. 28, 2010, 1-10). Without being bound by theory, inhibitors of the PI3K signaling cascade are useful for the treatment of cellular proliferative diseases.

As used herein, the term "patient" refers to a mammal, preferably a human.

In one aspect, provided herein is a method for the treatment of disorders mediated by PI3K, comprising administering to a patient in need of such treatment an effective amount of a crystalline compound of formula I, especially polymorph form $S_A$, $S_B$, $S_C$, or $S_D$.

In one embodiment of the method, the PI3K is PI3Kα.

In another embodiment of the method, the disorder is a cellular proliferative disease.

In yet another embodiment of the method, the disorder is selected from: benign or malignant tumor, or is a cancer selected from: sarcoma, lung, bronchus, prostate, breast (including sporadic breast cancers and sufferers of Cowden disease), pancreas gastrointestinal cancer, colon, rectum, colon carcinoma, colorectal adenoma, thyroid, liver, intrahepatic bile duct, hepatocellular, adrenal gland, stomach, gastric, glioma, glioblastoma, endometrial, melanoma, kidney, renal pelvis, urinary bladder, uterine corpus, uterine cervix, vagina, ovary, multiple myeloma, esophagus; a leukaemia; acute myelogenous leukemia; chronic myelogenous leukemia; lymphocytic leukemia, myeloid leukemia, brain, a carcinoma of the brain, oral cavity and pharynx, larynx, small intestine, non-Hodgkin lymphoma, melanoma, villous colon adenoma, a neoplasia, a neoplasia of epithelial character, lymphomas, a mammary carcinoma, basal cell carcinoma, squamous cell carcinoma, actinic keratosis, tumor diseases, including solid tumors, a tumor of the neck or head, polycythemia vera, essential thrombocythemia, myelofibrosis with myeloid metaplasia, and Walden stroem disease.

In still another embodiment of the method, the disorder is selected from polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g., haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In one aspect, provided herein is a method for the treatment of the disorders listed above, comprising administering to a patient in need of such treatment an effective amount of a crystalline compound of formula I, especially polymorph form $S_A$, $S_B$, $S_C$, or $S_D$. In another aspect, provided herein is a method for the treatment of a cellular proliferative disease comprising administering to a patient in need of such treatment an effective amount of a compound of formula I having polymorph form $S_A$, $S_B$, $S_C$, or $S_D$. The cellular proliferative disease can be selected from: benign or malignant tumor, or is a cancer selected from: sarcoma, lung, bronchus, prostate, breast (including sporadic breast cancers and sufferers of Cowden disease), pancreas gastrointestinal cancer, colon, rectum, colon carcinoma, colorectal adenoma, thyroid, liver, intrahepatic bile duct, hepatocellular, adrenal gland, stomach, gastric, glioma, glioblastoma, endometrial, melanoma, kidney, renal pelvis, urinary bladder, uterine corpus, uterine cervix, vagina, ovary, multiple myeloma, esophagus; a leukaemia; acute myelogenous leukemia; chronic myelogenous leukemia; lymphocytic leukemia, myeloid leukemia, brain, a carcinoma of the brain, oral cavity and pharynx, larynx, small intestine, non-Hodgkin lymphoma, melanoma, villous colon adenoma, a neoplasia, a neoplasia of epithelial character, lymphomas, a mammary carcinoma, basal cell carcinoma, squamous cell carcinoma, actinic keratosis, tumor diseases, including solid tumors, a tumor of the neck or head, polycythemia vera, essential thrombocythemia, myelofibrosis with myeloid metaplasia, and Walden stroem disease.

In still another aspect, provided herein is a method for the treatment of polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g., haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma, comprising administering to a patient in need of such treatment an effective amount of a compound of formula I having polymorph form $S_A$, $S_B$, $S_C$, or $S_D$.

The present invention also provides for the use of a crystalline compound of formula I, especially polymorph form $S_A$, $S_B$, $S_C$, or $S_D$, for the preparation of a medicament for the prevention, amelioration or treatment of conditions, disorders or diseases mediated by the activation of PI3K, especially PI3Kα.

In one aspect, provided herein is the use of a crystalline compound of formula I, especially polymorph form $S_A$, $S_B$, $S_C$, or $S_D$, for the preparation of a medicament for the treatment of disorders mediated by PI3K. In one embodiment of the use, the disorder is a cellular proliferative disease, such as the disorders listed above. In another aspect, provided herein is the use of a crystalline compound of formula I, especially polymorph form $S_A$, $S_B$, $S_C$, or $S_D$, for the preparation of a medicament for the treatment of the disorders listed above.

Pharmaceutical Compositions

The compounds of the present invention are suitable as active agents in pharmaceutical compositions that are efficacious particularly for treating protein kinase-associated disorders, especially PI3K-associated disorders, e.g., cancer. The pharmaceutical composition in various embodiments has a pharmaceutically effective amount of the crystalline compound of formula I, especially the polymorph form $S_A$, $S_B$, $S_C$, or $S_D$, along with other pharmaceutically acceptable excipients, carriers, fillers, diluents and the like.

The language "pharmaceutically effective amount" or "pharmaceutically acceptable amount" of the compound is that amount necessary or sufficient to treat or prevent a PI3K-associated disorder, e.g., prevent the various morphological and somatic symptoms of a protein kinase-associated disorder, especially a PI3K-associated disorder, and/or a disease or condition described herein. In an example, an effective amount of a compound of the invention is the amount sufficient to treat a PI3K-associated disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes a pharmaceutically effective amount. A compound of the invention can be administered to the subject either prior to or after the onset of a PI3K-associated disorder. Further, several divided dosages, as well as staggered dosages can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

In one non-limiting embodiment, the phrase "pharmaceutically effective amount" refers to the amount of a compound of the present invention that, when administered to a subject, is effective to (1) at least partially alleviate, ameliorate, inhibit, prevent and/or treat a condition, or a disorder or a disease (i) mediated PI3K, or (ii) associated with PI3K, or (iii) characterized by abnormal activity of PI3K; or (2) reduce or inhibit the activity of PI3K; or (3) reduce or inhibit the expression of PI3K. In still another non-limiting embodiment, the term "pharmaceutically effective amount" refers to the amount of a compound of the present invention that, when administered to a cell, or a tissue, or a non-cellular biological material, or a medium, is effective to at least partially reduce or inhibit the activity of PI3K; or at least partially reduce or inhibit the expression of PI3K.

The effective amount can vary depending on such factors as the size and weight of the subject, the type of illness, or the particular organic compound. For example, the choice of the organic compound can affect what constitutes an "effective amount." One of ordinary skill in the art would be able to study the aforementioned factors and make the determination regarding the acceptable amount of the organic compound without undue experimentation.

Compounds of the invention may be used in the treatment of states, disorders or diseases as described herein, or for the manufacture of pharmaceutical compositions for use in the treatment of these diseases. Methods of use of compounds of the present invention include the treatment of these diseases, and the manufacture of pharmaceutical preparations comprising compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a PI3K-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The present pharmaceutical compositions comprise one or more pharmacologically active substances. Thus, in one aspect, provided herein is a pharmaceutical composition comprising a crystalline compound of formula I.

In another aspect, provided herein is a the pharmaceutical composition comprising the polymorph form $S_A$, and a pharmaceutically acceptable carrier or diluent. In another embodiment, the pharmaceutical composition comprising the polymorph form $S_B$, and a pharmaceutically acceptable carrier or diluent. In yet another embodiment, the pharmaceutical composition comprising the polymorph form $S_C$, and a pharmaceutically acceptable carrier or diluent. In still another embodiment, the pharmaceutical composition comprising the polymorph form $S_D$, and a pharmaceutically acceptable carrier or diluent.

In one embodiment, the pharmaceutical composition comprises less than 0.1% by weight of polymorph form $S_A$, $S_B$, $S_C$, or $S_D$ based on the total weight of the compound of formula I in the composition. In another embodiment, the pharmaceutical composition comprises less than 1% by weight of polymorph form $S_A$, $S_B$, $S_C$, or $S_D$ based on the total weight of the compound of formula I in the composition. In yet another embodiment, the pharmaceutical composition comprises less than 10.0% by weight of polymorph form $S_A$, $S_B$, $S_C$, or $S_D$ based on the total weight of the compound of formula I in the composition. In still another embodiment, the pharmaceutical composition comprises less than 50.0% by weight of polymorph form $S_A$, $S_B$, $S_C$, or $S_D$ based on the total weight of the compound of formula I in the composition. In another embodiment, the pharmaceutical composition comprises at least 50.0% by weight of polymorph form $S_A$, $S_B$, $S_C$, or $S_D$ based on the total weight of the compound of formula I in the composition. In yet another embodiment, the pharmaceutical composition comprises at least 75.0% by weight of polymorph form $S_A$, $S_B$, $S_C$, or $S_D$ based on the total weight of the compound of formula I in the composition. In still another embodiment, the pharmaceutical composition comprises at least 99.0% by weight of polymorph form $S_A$, $S_B$, $S_C$, or $S_D$ based on the total weight of the compound of formula I in the composition. In yet another embodiment, the pharmaceutical composition comprises at least 99.9% by weight of polymorph form $S_A$, $S_B$, $S_C$, or $S_D$ based on the total weight of the compound of formula I in the composition.

In one embodiment, the pharmaceutical composition is formulated for oral administration. In another embodiment, the pharmaceutical composition is formulated for parenteral administration. In yet another embodiment, the pharmaceutical composition is formulated for topical administration.

Kits

The present invention also provides kits for use by a consumer for treating disease. The kits comprise a) a pharmaceutical composition comprising a crystalline compound of formula I and a pharmaceutically acceptable carrier, vehicle or diluent; and, optionally, b) instructions describing a method of using the pharmaceutical composition for treating the specific disease. Representative kits include a PI3K inhibitor compound (e.g., a crystalline compound of formula I) and a package insert or other labeling including directions for treating a cellular proliferative disease by administering a PI3K inhibitory amount of the compound(s).

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

EXEMPLIFICATION OF THE INVENTION

Scheme 1. Synthesis of (S)-Pyrrolidine-1,2-dicarboxylic acid 2-amide 1-{[5-(2-tert-butyl-pyridin-4-yl)-4-methyl-thiazol-2-yl]-amide}

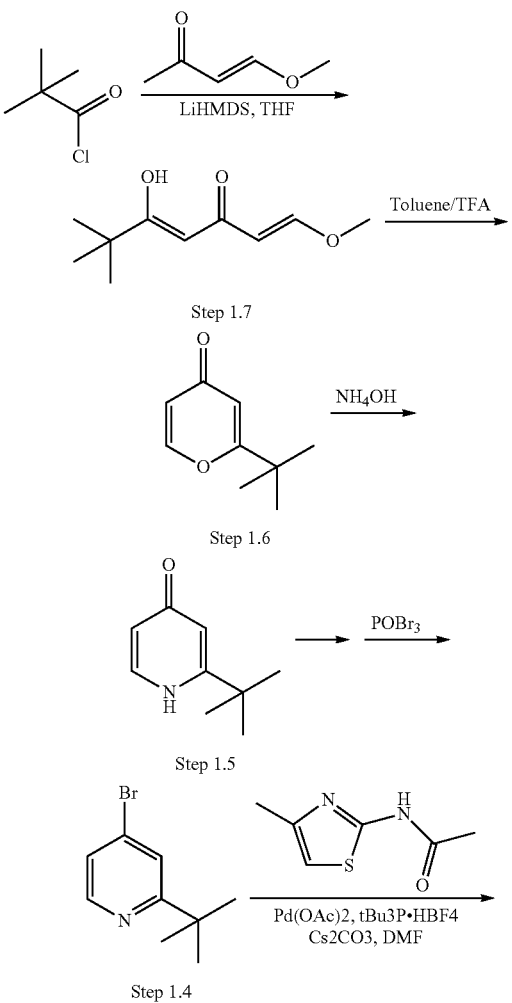

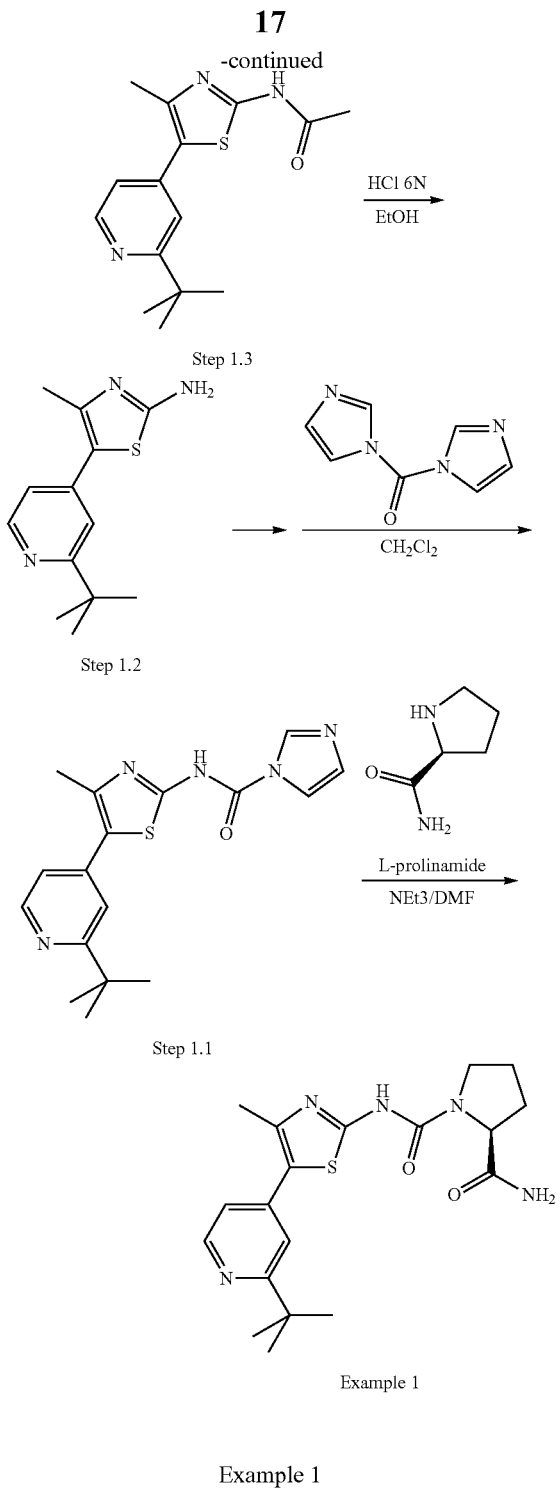

Example 1

Synthesis of (S)-Pyrrolidine-1,2-dicarboxylic acid 2-amide 1-{[5-(2-tert-butyl-pyridin-4-yl)-4-methyl-thiazol-2-yl]-amide}

Triethylamine (1.54 mL, 11.1 mmol, 3 eq) is added to a solution of imidazole-1-carboxylic acid [5-(2-tert-butyl-pyridin-4-yl)-4-methyl-thiazol-2-yl]-amide (Step 1.1) (1.26 g, 3.7 mmol) and L-prolinamide (0.548 g, 4.8 mmol, 1.3 eq) in DMF (25 mL), under an argon atmosphere. The reaction mixture is stirred for 14 h at rt, quenched by addition of a saturated solution of NaHCO3, and extracted with EtOAc. The organic phase is washed with a saturated solution of NaHCO3, dried (Na2SO4), filtered and concentrated. The residue is purified by silica gel column chromatography (DCM/MeOH, 1:0→94:6), followed by trituration in Et2O to afford 1.22 g of the title compound as an off-white solid: ESI-MS: 388.1 [M+H]+; tR=2.35 min (System 1); TLC: Rf=0.36 (DCM/MeOH, 9:1).

Step 1.1: Imidazole-1-carboxylic acid [5-(2-tert-butyl-pyridin-4-yl)-4-methyl-thiazol-2-yl]-amide A mixture of 5-(2-tert-butyl-pyridin-4-yl)-4-methyl-thiazol-2-ylamine (Step 1.2) (1 g, 4.05 mmol) and 1,1'-carbonyl-diimidazole (0.984 g, 6.07 mmol, 1.5 eq) in DCM (50 mL) is stirred for 4 h at reflux and allowed to cool. The resulting precipitate is collected by filtration to provide 1.26 g of the title compound as white solid: ESI-MS: 340.2 [M−H]−; tR=2.85 min (System 1).

Step 1.2: 5-(2-tert-Butyl-pyridin-4-yl)-4-methyl-thiazol-2-ylamine

A mixture of N-[5-(2-tert-butyl-pyridin-4-yl)-4-methyl-thiazol-2-yl]-acetamide (Step 1.3) (2 g, 7 mmol), a 6N aqueous solution of HCl (10 mL) and EtOH (50 mL) is stirred for 2 h at 85° C., allowed to cool, quenched by addition of a saturated solution of NaHCO3 and extracted with DCM/MeOH (9:1, v/v). The organic phase is washed with a saturated solution of NaHCO3, dried (Na2SO4), filtered and concentrated. The residue is purified by silica gel column chromatography (DCM/MeOH, 1:0→96:4) to afford 1.21 g of the title compound as a yellow solid: ESI-MS: 248.1 [M+H]+; TLC: Rf=0.36 (DCM/MeOH, 9:1).

Step 1.3: N-[5-(2-tert-Butyl-pyridin-4-yl)-4-methyl-thiazol-2-yl]-acetamide

A mixture of 2-acetamido-4-methylthiazole (1.2 g, 7.7 mmol, 1.1 eq), cesium carbonate (4.55 g, 14 mmol, 2 eq), tri-tert-butylphosphinium tetrafluoroborate (0.406 g, 1.4 mmol, 0.2 eq), palladium (II) acetate (0.15 g, 0.7 mmol, 0.1 eq) and 4-bromo-2-tert-butyl-pyridine (Step 1.4) (1.5 g, 7 mmol) in DMF (50 mL) is stirred for 1.5 h at 90° C. under an argon atmosphere, allowed to cool, quenched by addition of a saturated solution of NaHCO3 and filtered through a pad of celite. The filtrate is extracted with EtOAc. The organic phase is washed with a saturated solution of NaHCO3, dried (Na2SO4), filtered and concentrated. The residue is purified by silica gel column chromatography (DCM/MeOH, 1:0→97:3) to afford 2.02 g of the title compound as a yellow solid: ESI-MS: 290.1 [M+H]+; TLC: Rf=0.35 (DCM/MeOH, 9:1).

Step 1.4: 4-Bromo-2-tert-butyl-pyridine

A mixture of 2-tert-butyl-1H-pyridin-4-one (Step 1.5) (4.25 g, 28 mmol) and POBr3 (8.88 g, 31 mmol, 1.1 eq) is heated to 120° C., stirred for 15 min, allowed to cool, quenched by addition of a saturated solution of NaHCO3 and extracted with DCM/MeOH (9:1, v/v). The organic phase is washed with a saturated solution of NaHCO3, dried (Na2SO4), filtered and concentrated. The residue is purified by silica gel column chromatography (Hex/EtOAc, 95:5) to afford 5.18 g of the title compound as a yellow oil: ESI-MS: 214.0/216.0 [M+H]+; tR=2.49 min (System 1); TLC: Rf=0.35 (Hex/EtOAc, 1:1).

Step 1.5: 2-tert-Butyl-1H-pyridin-4-one

A mixture of 2-tert-butyl-pyran-4-one (Step 1.6) (5.74 g, 37.7 mmol) and a 30% aqueous solution of ammonium hydroxide (100 mL) is stirred for 1 h at reflux, allowed to cool and concentrated. The residue is triturated with MeOH (200 mL) and filtered. The filtrate is concentrated and the residue purified by silica gel column chromatography (DCM/MeOH/NH3aq, 94:5:1→92:7:1) to afford 4.46 g of the title compound as a yellow solid: ESI-MS: 152.0 [M+H]+; tR=1.45 min (System 1); TLC: Rf=0.11 (DCM/MeOH, 9:1).

Step 1.6: 2-tert-Butyl-pyran-4-one

A mixture of 5-hydroxy-1-methoxy-6,6-dimethyl-hepta-1,4-dien-3-one (Step 1.7) (6.8 g, 36.9 mmol) and TFA (5.65 mL, 74 mmol, 2 eq) in benzene (250 mL) is stirred for 14 h at rt and concentrated. Purification of the residue by silica gel column chromatography (Hex/EtOAc, 1:0-+75:25) provides 5.74 g of the title compound as a yellow oil: ESI-MS: 153.1 [M+H]+; tR=3.21 min (System 1); TLC: Rf=0.22 (Hex/EtOAc, 1:1).

Step 1.7: 5-Hydroxy-1-methoxy-6,6-dimethyl-hepta-1,4-dien-3-one

LiHMDS (1M in THF, 100 mL, 2 eq) is added dropwise to a cold (−78° C.) solution of 4-methoxy-3-buten-2-one (10 mL, 100 mmol, 2 eq) in THF (400 mL). After a 30 min stirring at −78° C., a solution of pivaloyl chloride (6.12 mL, 50 mmol) in THF (100 mL) is added. The resulting mixture is allowed to warm to rt over 2 h and quenched by addition of a saturated solution of NH4Cl. THF is removed under vacuum. The concentrated mixture is extracted with Et2O. The organic phase is washed with brine, dried (Na2SO4), filtered and concentrated. The residue is purified by silica gel column chromatography (Hex/EtOAc, 1:0→85:15) to afford 6.83 g of the title compound as a yellow oil: ESI-MS: 185.1 [M+H]+; TLC: Rf=0.87 (Hex/EtOAc, 1:1).

Scheme 2. Synthesis of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide)

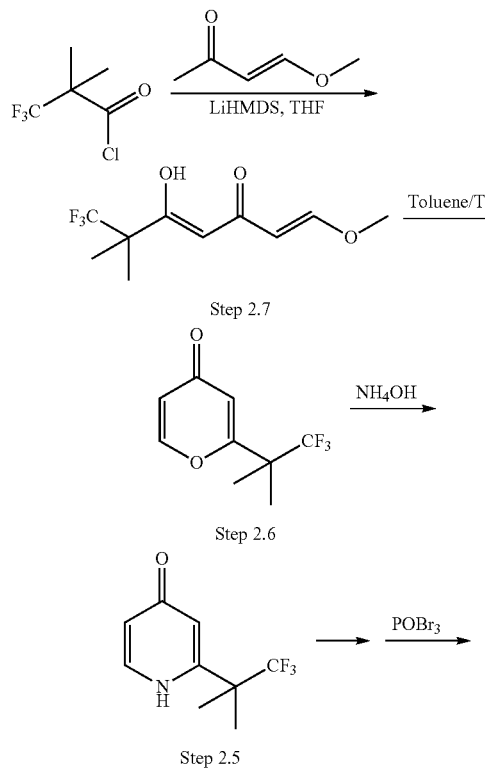

Example 2

(S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide)

The title compound is prepared in analogy to the procedure described in Example 1 but with the following modifications. In Step 2.1 (corresponding to Step 1.1 of Example 1), the reaction mixture is stirred for 14 h at reflux. In Step 2.2 (corresponding to Step 1.2 of Example 1), the reaction mixture is stirred for 1 h at 85° C. and extracted with ethyl acetate after being quenched. In step 2.3 (corresponding to Step 1.3 of Example 1), the reaction mixture is stirred for 2.5 h at 120° C. In Step 2.4 (corresponding to Step 1.4 of Example 1), the reaction mixture is stirred for 1 h at 83° C. and extracted with ethyl acetate after being quenched. In Step 2.5 (corresponding to Step 1.5 of Example 1), the reaction mixture is stirred for 1 h at 65° C. and trituration in methanol is not performed. In Step 2.6 (corresponding to Step 1.6 of Example 1), the crude product is not purified. In Step 2.7 (corresponding to Step 1.7 of Example 1), 3,3,3-trifluoro-2,2-dimethyl-propionyl chloride is used.

Title compound: ESI-MS: 442.0 [M+H]$^+$; $t_R$=3.02 min (System 1); TLC: $R_f$=0.35 (DCM/MeOH, 9:1).

Example 3

Preparation of Polymorph Form A (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (10.0 g) was suspended in ethanol/water (85:15 v/v; 75 mL) and the mixture was heated to 75° C. The solution was clear-filtered into a second flask and the first flask was then washed with ethanol/water (4:6 v/v; 20 mL), followed by water (10 mL). The clear solution was stirred at 75° C. for an additional 30 minutes. The clear solution was then cooled to 2° C. over 2 hours and the obtained thick suspension was stirred at 2° C. for an additional hour. The mixture was then filtered, and the flask and filter cake were washed with ethanol/water (1:1 v/v; 20 mL), followed by ethyl acetate (10 mL). The wet filter cake was returned to the flask and suspended in ethyl acetate (75 mL). the mixture was heated to 78° C. and was stirred under reflux for 1 hour. During this time, 15 mL ethyl acetate was distilled off. The mixture was then cooled to 2° C. over 2 hours and the suspension was stirred at 2° C. for an additional hour. The mixture was filtered, and the flask and filter cake were washed with cold ethyl acetate (12 mL). The filter cake was then dried under 1-50 mbar vacuum at 50° C. to yield the polymorph form A (7.3 g).

Example 4

Preparation of Polymorph Form $S_A$

The polymorph form A of Compound 1 (800 mg) was added to a mixture of 1.5 g water and 3.5 g acetone and stirred constantly in a vial at 20° C. for 90 hours. Solid polymorph form $S_A$ was collected by filtration. The product was analyzed by X-ray powder diffractometry, resulting in the pattern depicted in FIG. 4.

Example 5

Preparation of Polymorph Form $S_B$

The polymorph form A of Compound I was equilibrated in ethanol or ethanol/water (1:1) solvent mixture at 25° C. for 24 hours. Solid polymorph form $S_B$ was collected by filtration. The product was analyzed by X-ray powder diffractometry, resulting in the pattern depicted in FIG. 5.

Example 6

Preparation of Polymorph Form $S_C$

The polymorph form A of Compound 1 (300 mg) was added to 5 g isopropanol and stirred constantly in a vial at 60° C. for 1 week. Solid polymorph form $S_C$ was collected by filtration. The product was analyzed by X-ray powder diffractometry, resulting in the pattern depicted in FIG. 6.

Example 7

Preparation of Polymorph Form $S_D$

The polymorph form A of Compound 1 was equilibrated in tetrahydrofurn at 25° C. for 24 hours. Solid polymorph form $S_D$ was collected by filtration. The product was analyzed by X-ray powder diffractometry, resulting in the pattern depicted in FIG. 7.

Tables

TABLE 1

List of most significant peaks of FIG. 1 (Polymorph Form A)

| 2-Theta in deg | Intensity in % |
| --- | --- |
| 4.2 | 79 |
| 8.5 | 19 |
| 9.3 | 25 |
| 10.5 | 13 |
| 15.5 | 12 |
| 16.8 | 36 |
| 17.1 | 100 |
| 18.2 | 36 |
| 20.1 | 54 |
| 20.4 | 87 |
| 21.0 | 34 |
| 21.3 | 27 |
| 21.7 | 50 |
| 22.7 | 10 |
| 24.9 | 10 |
| 25.1 | 15 |
| 25.6 | 11 |
| 26.2 | 20 |
| 26.5 | 16 |
| 27.0 | 33 |
| 27.9 | 10 |
| 31.2 | 11 |
| 33.0 | 11 |

The strongest line in the pattern is observed at an angle of diffraction of 2-Theta of 17.1° and has a relative intensity of 100%. X-ray powder diffraction measurement was obtained using a Bruker X-ray diffractometer with a CuKα radiation source; Step: 0.017°; Range: 2.00°-40.00°; Constant scan rate: 0.3 s/step; All 2-Theta values +/−0.3°.

TABLE 2

Figure 4:
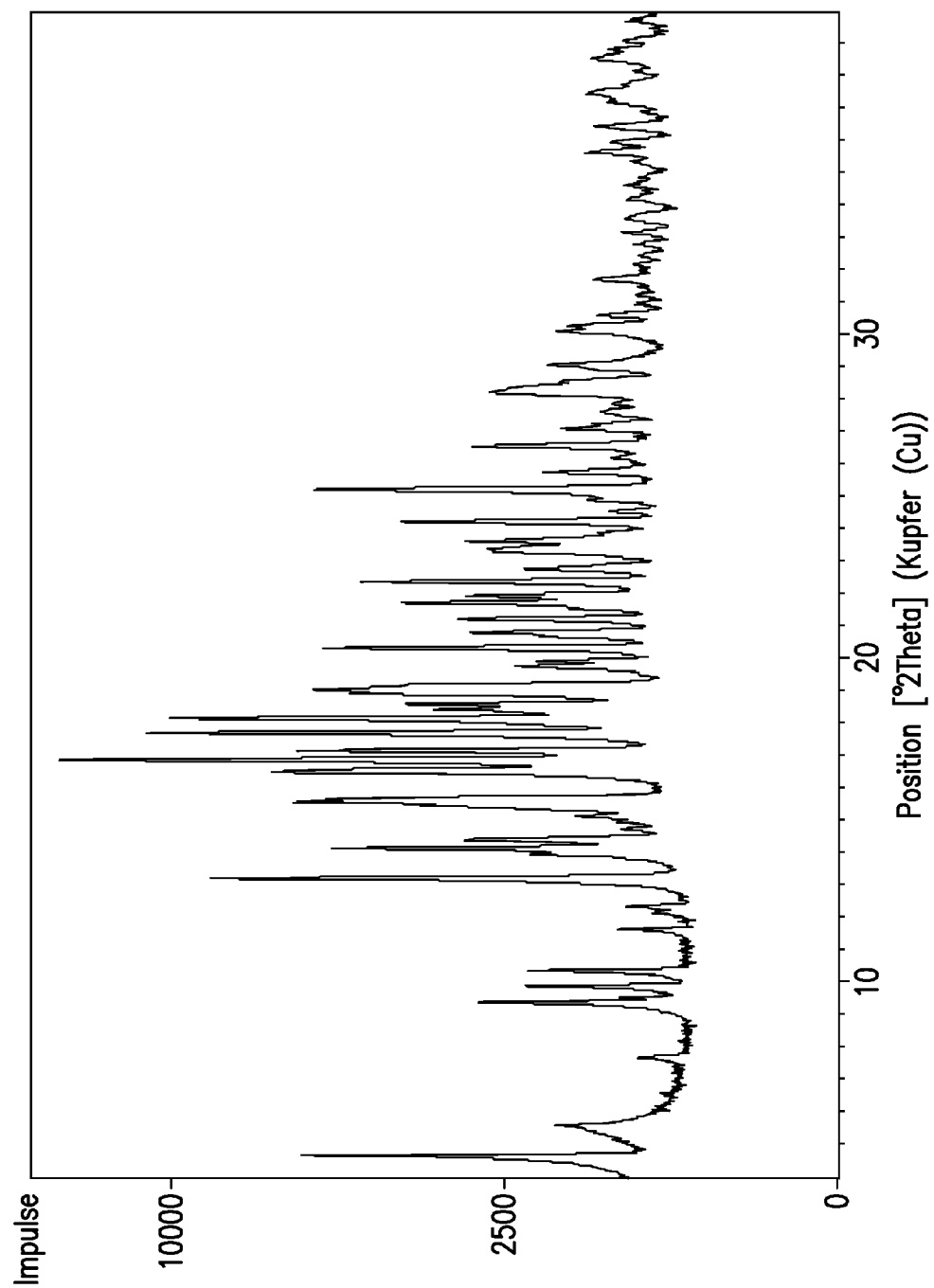
FIG. 4 (also referenced as FIG. IV) depicts the X-ray powder diffraction pattern of polymorph form $S_A$.

List of most significant peaks of FIG. 4 (Polymorph Form $S_A$)

| 2-Theta in deg | Intensity in % |
| --- | --- |
| 4.7 | 36 |
| 9.4 | 17 |
| 9.9 | 12 |
| 10.4 | 11 |
| 13.3 | 59 |

TABLE 2-continued

List of most significant peaks of FIG. 4 (Polymorph Form $S_A$)

| 2-Theta in deg | Intensity in % |
| --- | --- |
| 14.2 | 37 |
| 14.4 | 18 |
| 15.7 | 36 |
| 16.5 | 47 |
| 16.9 | 100 |
| 17.2 | 43 |
| 17.7 | 73 |
| 18.2 | 68 |
| 18.4 | 22 |
| 18.6 | 26 |
| 18.9 | 33 |
| 19.2 | 29 |
| 20.3 | 38 |
| 20.8 | 17 |
| 21.2 | 19 |
| 21.7 | 26 |
| 21.9 | 18 |
| 22.4 | 33 |
| 23.3 | 14 |
| 23.6 | 18 |
| 24.2 | 26 |
| 25.2 | 40 |

The strongest line in the pattern is observed at an angle of diffraction of 2-Theta of 16.9° and has a relative intensity of 100%. X-ray powder diffraction measurement was obtained using a Bruker X-ray diffractometer with a CuKα radiation source; Step: 0.017°; Range: 2.00°-40.00°; Constant scan rate: 0.3 s/step; All 2-Theta values +/−0.3°.

TABLE 3

Figure 5:
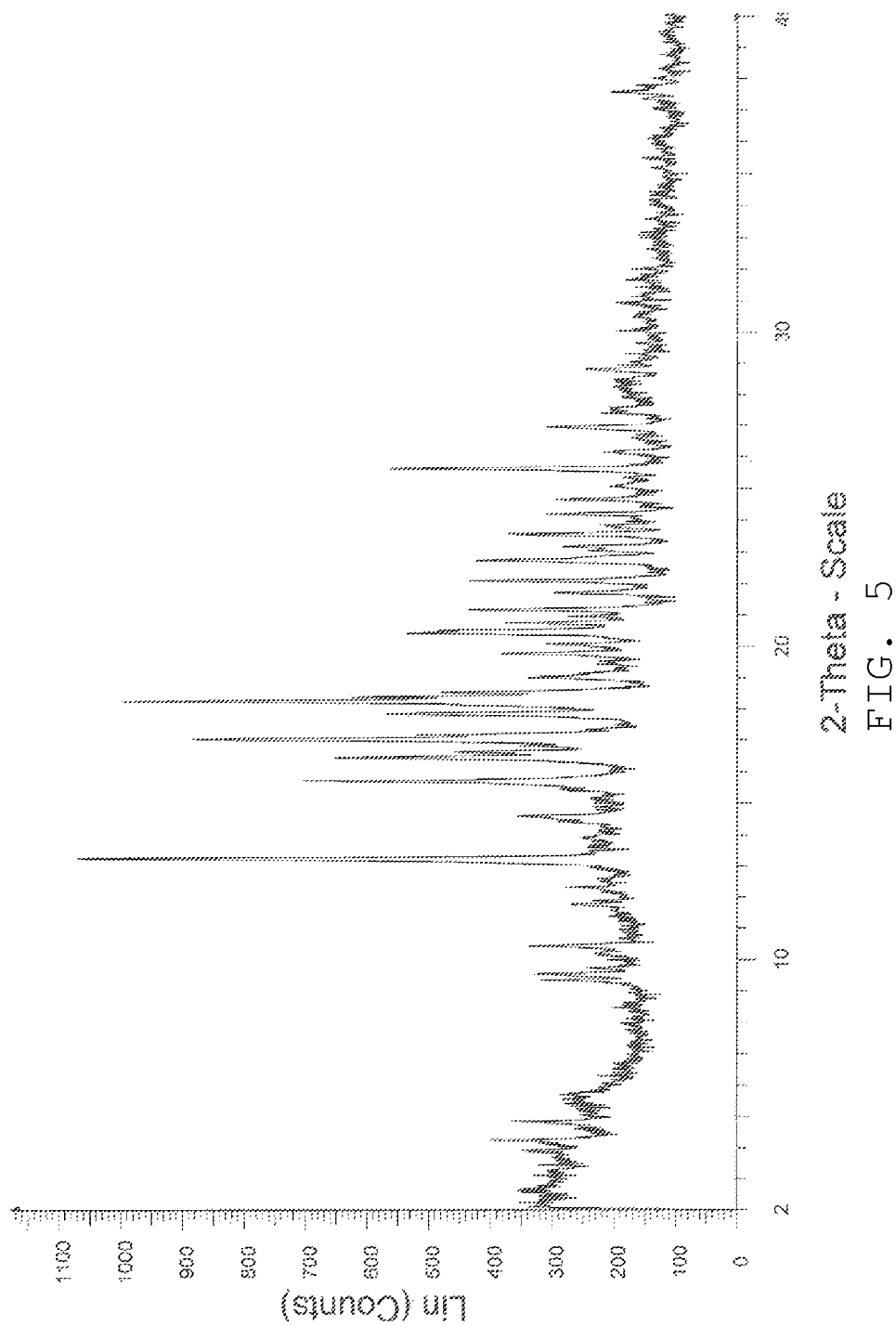
FIG. 5 (also referenced as FIG. V) depicts the X-ray powder diffraction pattern of polymorph form $S_B$.

List of most significant peaks of FIG. 5 (Polymorph Form $S_B$)

| 2-Theta in deg | Intensity in % |
| --- | --- |
| 4.2 | 21 |
| 9.3 | 19 |
| 9.5 | 20 |
| 10.4 | 20 |
| 13.2 | 100 |
| 15.7 | 57 |
| 16.4 | 52 |
| 16.6 | 30 |
| 17.0 | 80 |
| 17.2 | 38 |
| 17.8 | 45 |
| 18.3 | 95 |
| 18.4 | 53 |
| 18.5 | 36 |
| 19.0 | 21 |
| 19.8 | 27 |
| 20.4 | 45 |
| 20.8 | 28 |
| 21.2 | 35 |
| 21.7 | 20 |
| 22.1 | 36 |
| 22.8 | 35 |
| 23.6 | 29 |
| 24.2 | 22 |
| 24.7 | 21 |
| 25.6 | 52 |

The strongest line in the pattern is observed at an angle of diffraction of 2-Theta of 13.2° and has a relative intensity of 100%. X-ray powder diffraction measurement was obtained using a Bruker X-ray diffractometer with a CuKα radiation source; Step: 0.017°; Range: 2.00°-40.00°; Constant scan rate: 0.3 s/step; All 2-Theta values +/−0.3°.

TABLE 4

Figure 6:
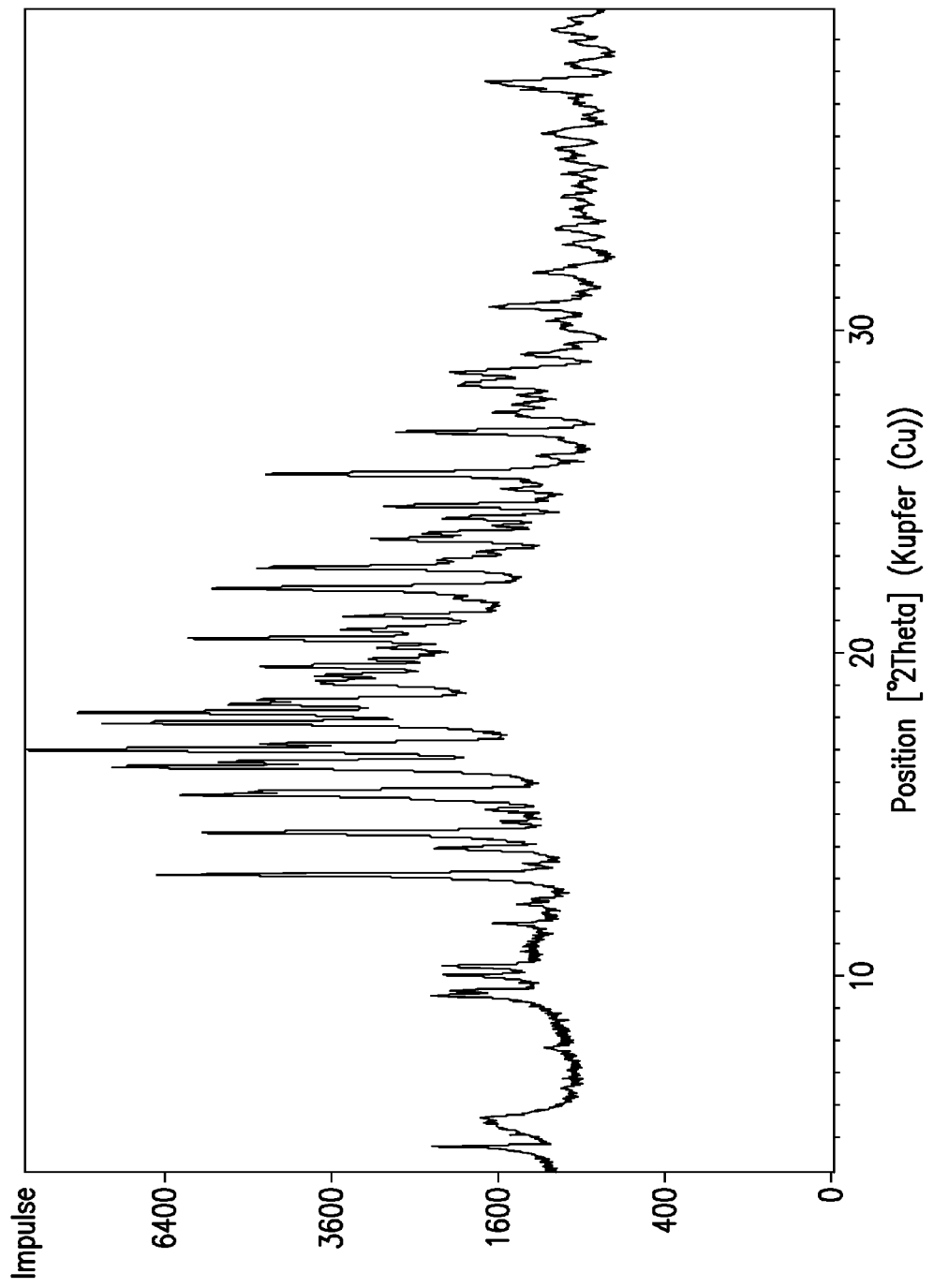
FIG. 6 (also referenced as FIG. VI) depicts the X-ray powder diffraction pattern of polymorph form $S_C$.

List of most significant peaks of FIG. 6 (Polymorph Form $S_C$)

| 2-Theta in deg | Intensity in % |
| --- | --- |
| 4.8 | 16 |
| 9.5 | 15 |
| 10.4 | 14 |
| 13.2 | 65 |
| 14.0 | 15 |
| 14.5 | 55 |
| 15.6 | 58 |
| 15.8 | 45 |
| 16.5 | 77 |
| 16.7 | 52 |
| 17.0 | 100 |
| 17.2 | 44 |
| 17.9 | 79 |
| 18.2 | 86 |
| 18.4 | 50 |
| 18.6 | 44 |
| 19.1 | 33 |
| 19.3 | 34 |
| 19.6 | 45 |
| 19.8 | 25 |
| 20.5 | 58 |
| 20.8 | 31 |
| 21.2 | 30 |
| 22.1 | 54 |
| 22.7 | 45 |
| 23.6 | 25 |
| 24.6 | 24 |

The strongest line in the pattern is observed at an angle of diffraction of 2-Theta of 17.0° and has a relative intensity of 100%. X-ray powder diffraction measurement was obtained using a Bruker X-ray diffractometer with a CuKα radiation source; Step: 0.017°; Range: 2.00°-40.00°; Constant scan rate: 0.3 s/step; All 2-Theta values +/−0.3°.

TABLE 5

Figure 7:
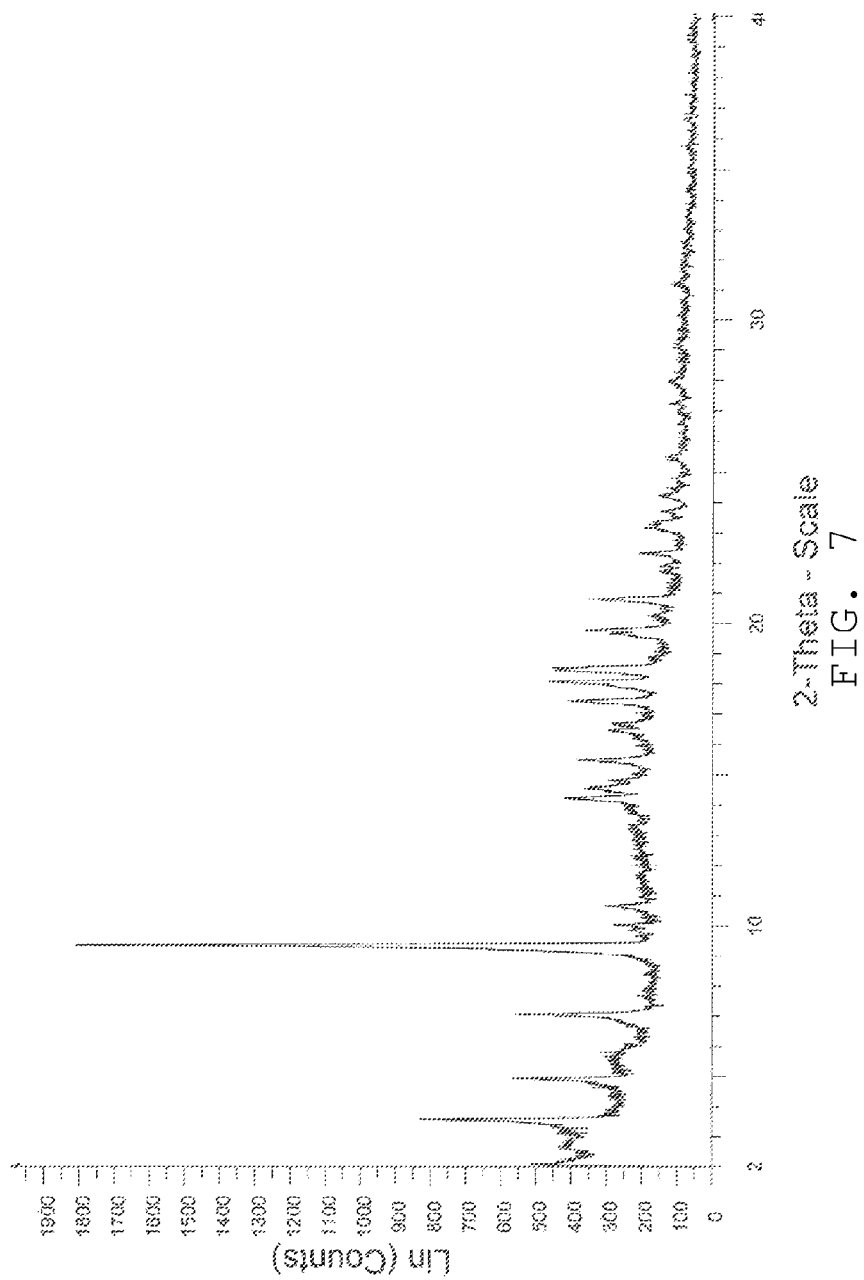
FIG. 7 (also referenced as FIG. VII) depicts the X-ray powder diffraction pattern of polymorph form $S_D$.

List of most significant peaks of FIG. 7 (Polymorph Form $S_D$)

| 2-Theta in deg | Intensity in % |
| --- | --- |
| 3.5 | 32 |
| 4.9 | 21 |
| 7.0 | 23 |
| 9.3 | 100 |
| 14.2 | 14 |
| 14.6 | 10 |
| 15.5 | 11 |
| 17.4 | 14 |
| 18.1 | 19 |
| 18.4 | 18 |
| 19.8 | 14 |
| 20.8 | 15 |

The strongest line in the pattern is observed at an angle of diffraction of 2-Theta of 9.3° and has a relative intensity of 100%. X-ray powder diffraction measurement was obtained using a Bruker X-ray diffractometer with a CuKα radiation source; Step: 0.017°; Range: 2.00°-40.00°; Constant scan rate: 0.3 s/step; All 2-Theta values +/−0.3°.

Biological Activity

The biological activity of the compound of formula I is described in WO 2010/029082. This compound demonstrated activity against the phosphatidylinositol 3-kinase (PI3K).

The invention claimed is:

1. A crystalline form of the compound of formula I,

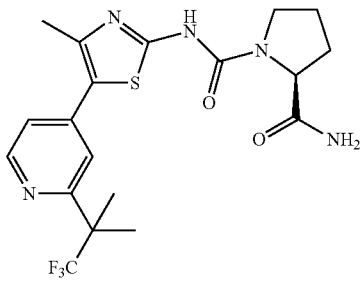

(I)

or a solvate of the crystalline form of the compound of formula I, or a salt of the crystalline form of the compound of formula I, or a solvate of a salt of the crystalline form of the compound of formula I, wherein said crystalline form of the compound of formula I is having polymorph form $S_A$, $S_B$, $S_C$, or $S_D$.

2. The crystalline form of the compound of claim 1, having the polymorph form $S_A$, wherein the polymorph exhibits an X-ray powder diffraction pattern having characteristic peaks expressed in degrees 2-Theta at angles of 16.9°+/−0.3° and 17.7°+/−0.3°.

3. The crystalline form of the compound according to claim 2, wherein the polymorph form $S_A$ exhibits an X-ray powder diffraction pattern having characteristic peaks expressed in degrees 2-Theta at angles of 16.9°+/−0.3°, 17.7°+/−0.3°, 13.3°+/−0.3°, 18.2°+/−0.3°, 20.3°+/−0.3° and 16.5°+/−0.3°.

4. The crystalline form of the compound according to claim 2, wherein the polymorph exhibits an X-ray powder diffraction pattern substantially in accordance with FIG. IV and Table 2.

5. The crystalline form of the compound of claim 1, having the polymorph form $S_B$, wherein the polymorph exhibits an X-ray powder diffraction pattern having characteristic peaks expressed in degrees 2-Theta at angles of 13.2°+/−0.3° and 18.3°+/−0.3°.

6. The crystalline form of the compound according to claim 5, wherein the polymorph form $S_B$ exhibits an X-ray powder diffraction pattern having characteristic peaks expressed in degrees 2-Theta at angles of 13.2°+/−0.3°, 18.3°+/−0.3°, 17.0°+/−0.3°, 15.7°+/−0.3°, 20.4°+/−0.3° and 16.4°+/−0.3°.

7. The crystalline form of the compound according to claim 5, wherein the polymorph exhibits an X-ray powder diffraction pattern substantially in accordance with FIG. V and Table 3.

8. The crystalline form of the compound of claim 1, having the polymorph form $S_C$, wherein the polymorph exhibits an X-ray powder diffraction pattern having characteristic peaks expressed in degrees 2-Theta at angles of 17.0°+/−0.3° and 18.2°+/−0.3°.

9. The crystalline form of the compound of according to claim 8, wherein the polymorph form $S_C$ exhibits an X-ray powder diffraction pattern having characteristic peaks expressed in degrees 2-Theta at angles of 17.0°+/−0.3°, 18.2°+/−0.3°, 16.5°+/−0.3°, 13.2°+/−0.3°, 14.5°+/−0.3° and 15.6°+/−0.3°.

10. The crystalline form of the compound according to claim 8, wherein the polymorph exhibits an X-ray powder diffraction pattern substantially in accordance with FIG. VI and Table 4.

11. The crystalline form of the compound of claim 1, having the polymorph form $S_D$, wherein the polymorph exhibits an X-ray powder diffraction pattern having characteristic peaks expressed in degrees 2-Theta at angles of 9.3°+/−0.3° and 3.5°+/−0.3°.

12. The crystalline form of the compound according to claim 11, wherein the polymorph form $S_D$ exhibits an X-ray powder diffraction pattern having characteristic peaks expressed in degrees 2-Theta at angles of 9.3°+/−0.3°, 3.5°+/−0.3°, 7.0°+/−0.3°, 4.9°+/−0.3°, 18.1°+/−0.3° and 20.8°+/−0.3°.

13. The crystalline form of the compound according to claim 11, wherein the polymorph exhibits an X-ray powder diffraction pattern substantially in accordance with FIG. VII and Table 5.

14. The pharmaceutical composition comprising the polymorph form $S_A$, $S_B$, Sc, or $S_D$ according to claim 1, and a pharmaceutically acceptable carrier or diluent.

15. A method for the treatment of melanoma, colorectal adenoma, and cancer of the breast and pancreas, comprising administering to a patient in need of such treatment an effective amount of the compound of claim 1.

* * * * *